(12) United States Patent
Ishida et al.

(10) Patent No.: US 9,999,434 B2
(45) Date of Patent: Jun. 19, 2018

(54) BRAKE MECHANISM AND MEDICAL MANIPULATOR PROVIDED WITH SAME

(71) Applicant: Karl Storz SE & Co. KG, Tuttlingen (DE)

(72) Inventors: Shinji Ishida, Fujinomiya (JP); Hiroaki Sano, Fujinomiya (JP); Tsuneyoshi Suzuki, Kanuma (JP); Junichi Fukuda, Kanuma (JP)

(73) Assignee: Karl Storz SE & Co. KG, Tuttlingen (DE)

( * ) Notice: Subject to any disclaimer, the term of this patent is extended or adjusted under 35 U.S.C. 154(b) by 457 days.

(21) Appl. No.: 14/669,866

(22) Filed: Mar. 26, 2015

(65) Prior Publication Data

US 2015/0196313 A1    Jul. 16, 2015

Related U.S. Application Data

(63) Continuation of application No. PCT/JP2013/075632, filed on Sep. 24, 2013.

(30) Foreign Application Priority Data

Sep. 26, 2012 (JP) .................................. 2012-212061

(51) Int. Cl.
*A61B 17/00* (2006.01)
*A61B 17/29* (2006.01)
(Continued)

(52) U.S. Cl.
CPC ............ *A61B 17/29* (2013.01); *A61B 17/062* (2013.01); *A61B 34/70* (2016.02); *A61B 34/71* (2016.02);
(Continued)

(58) Field of Classification Search
CPC .................. A61B 17/062; A61B 17/29; A61B 2017/00398; A61B 2017/2902;
(Continued)

(56) References Cited

U.S. PATENT DOCUMENTS 5,830,231 A    11/1998 Geiges, Jr.
6,139,413 A * 10/2000 Sirany .................... B24B 5/065
                                                    188/71.1
(Continued)

FOREIGN PATENT DOCUMENTS

JP    2004008367 A    1/2004
JP    2006326148 A    12/2006
(Continued)

OTHER PUBLICATIONS

Supplementary European Search Report, Application No. EP 13741694, Completed: Mar. 30, 2016; dated Apr. 8, 2016, 8 pages.

*Primary Examiner* — Elizabeth Houston
*Assistant Examiner* — Mohamed Gabr
(74) *Attorney, Agent, or Firm* — Whitmyer IP Group LLC

(57) ABSTRACT

A medical manipulator is provided with a brake mechanism. The brake mechanism is provided with a brake rotor and a brake shoe which can contact the outer periphery of the brake rotor. On the outer periphery of the brake rotor, a first gear is provided along the circumference. On the portion of the brake shoe which is opposite of the outer periphery of the brake rotor, a second gear is provided which can mesh with the first gear.

6 Claims, 12 Drawing Sheets

(51) Int. Cl.
    *F16D 49/16*     (2006.01)
    *F16D 63/00*     (2006.01)
    *A61B 17/062*     (2006.01)
    *A61B 34/00*     (2016.01)
    *A61B 90/50*     (2016.01)

(52) U.S. Cl.
    CPC ........... F16D 49/16 (2013.01); F16D 63/006 (2013.01); *A61B 2017/00398* (2013.01); *A61B 2017/2902* (2013.01); *A61B 2017/2927* (2013.01); *A61B 2017/2929* (2013.01); *A61B 2017/2946* (2013.01); *A61B 2017/2947* (2013.01); *A61B 2090/508* (2016.02)

(58) Field of Classification Search
    CPC .... A61B 2017/2927; A61B 2017/2929; A61B 2017/2946; A61B 2017/2947; A61B 2090/508; A61B 34/70; A61B 34/71; F16D 49/16; F16D 63/006

USPC .................................................. 188/74, 166
    See application file for complete search history.

(56) References Cited

U.S. PATENT DOCUMENTS

| | | |
|---|---|---|
| 2004/0225323 A1 | 11/2004 | Nagase et al. |
| 2006/0241655 A1* | 10/2006 | Viola .................. A61B 17/128 606/142 |
| 2008/0255608 A1* | 10/2008 | Hinman ................. A61B 17/29 606/205 |
| 2010/0057121 A1 | 3/2010 | Piskun et al. |
| 2010/0170931 A1 | 7/2010 | Viola |

FOREIGN PATENT DOCUMENTS

| | | |
|---|---|---|
| JP | 4391762 B2 | 12/2009 |
| JP | 2010099460 A | 5/2010 |
| WO | 2012006306 A2 | 1/2012 |

* cited by examiner

BRAKE MECHANISM AND MEDICAL MANIPULATOR PROVIDED WITH SAME

FIELD OF THE INVENTION

The present invention relates to a brake mechanism and a medical manipulator provided with the same for limiting movement of a mechanism linked operatively with a working unit, and by which operations with respect to a rotary operating member are transmitted mechanically.

BACKGROUND OF THE INVENTION

In an endoscopic surgical operation (also referred to as "laparoscopic surgery"), a plurality of holes are punctured in the abdomen or the like of a patient, trocars (cylindrical instruments) are inserted through the holes, and a laparoscope (camera) and a plurality of forceps are inserted into the body cavity via each of the trocars. Grippers for gripping biological tissue, scissors, and blades of an electrosurgical knife may be mounted to the tip of the forceps as an end effector.

The laparoscope and the forceps are inserted into the body cavity, and an operator then operates by operating the forceps while viewing a state of the inner portion of the abdominal cavity, which is shown on a monitor that is connected to the laparoscope. Since the surgical procedure does not require a laparotomy, the burden on the patient is decreased, which reduces the number of days for postoperative recovery and the number of days until the patient leaves the hospital. For this reason, the fields that such an operative method can be applied to are expected to expand.

Other than typical forceps that are not provided with joints at distal end portions thereof, as forceps that are used in an endoscopic surgical operation, forceps referred to as a medical manipulator have been developed that are provided with joints at distal end portions and which can carry out a rolling operation or a tilting operation of an end effector (for example, refer to Japanese Patent No. 4391762). In accordance with such a medical manipulator, a high degree of operational freedom is facilitated in the body cavity, manual procedures are made easy, and thus there are a large number of medical cases to which the medical manipulator may be applied.

SUMMARY OF THE INVENTION

Incidentally, in an operation using a medical manipulator equipped with a tiltable end effector, cases occur in which a biological tissue (e.g., an organ) is pressed by the end effector which is inserted into the living body. In this case, assuming that tilting of the end effector is carried out by a motor drive, due to rotational resistance of the motor and the presence of the gears or the like, even if a reaction force is received by the end effector from the living tissue, a change in the angle of the end effector caused by such a reaction force is suppressed. However, if an operating member (operating dial) is manually operated to carry out tilting of the end effector, in the event that the living tissue is pressed by the end effector, the angle of the end effector still tends to be changed by such a reaction force.

In order to prevent such an occurrence, it may be possible to ensure that the end effector does not undergo movement by holding the operating member firmly with hand. However, such an action is troublesome, and carrying out procedures is difficult. Further, for ensuring that the end effector does not undergo movement due to such reaction forces, it may be considered to arrange a worm gear in the power transmission path between the operating member and the end effector. However, when such a worm gear is used, it becomes necessary for the operating member to be turned many times in order to change the angle of the end effector, and responsiveness to operations of the operating member is deteriorated.

Further, in the medical manipulator, a brake mechanism is adopted, which exerts a braking force by a brake rotor and a brake shoe. At the time that the braking force is exerted, the brake shoe is pressed against the brake rotor due to an elastic force of an elastic member such as a spring or the like, and by a frictional force occurring at that time, the braking force is exerted. In addition, a structure is conceived of in which the braking action is released by separating the brake shoe away from the brake rotor in opposition to the elastic force.

However, if the elastic force of the elastic member is small, the frictional force developed between the brake rotor and the brake shoe also is small, and a sufficient braking force cannot be obtained, such that when the end effector presses against a living tissue, the angle of the end effector cannot be maintained. Conversely, if the elastic force of the elastic member is too large, the operating force needed to release the braking action becomes large as well, and operability of the medical manipulator is adversely affected.

The present invention has been devised while taking into consideration the aforementioned problems, and has the object of providing a brake mechanism which is capable of producing a large braking force while reducing an elastic force for pressing a brake shoe against a brake rotor, and a medical manipulator equipped with such a brake mechanism.

For achieving the aforementioned object, a brake mechanism according to the present invention restricts movement of a mechanism linked operatively with a working unit, and by which an input operation with respect to an operating member is transmitted mechanically, the brake mechanism including a brake rotor that rotates in conjunction with rotation of the operating member, a brake shoe, which is capable of advancing and retracting with respect to the brake rotor, and is capable of contacting an outer circumference of the brake rotor, wherein based on an elastic force of an elastic member, the brake shoe is pressed against the brake rotor to thereby generate a braking force; a braking action is released by separating the brake shoe away from the brake rotor in opposition to the elastic force, a first gear is disposed along a circumferential direction on the outer circumference of the brake rotor, and a second gear, which is capable of meshing with the first gear, is disposed on a portion of the brake shoe that confronts the outer circumference of the brake rotor.

According to the above structure, when the brake shoe is pressed against the brake rotor based on the elastic force of the elastic member, the first gear provided on the brake rotor and the second gear provided on the brake shoe enmesh with each other. Therefore, compared to a situation in which the outer circumference of the brake rotor and the brake shoe are both smooth surfaces, due to intermeshing of the gears, a stronger braking force can be obtained. Consequently, even if the elastic force of the elastic member is small, a sufficient braking force can be obtained, and thus the operating force when braking is released in opposition to the elastic force of the elastic member can effectively be reduced.

The above-described brake mechanism may further include a slide member, which is elastically pressed by the elastic member toward the brake rotor, and is capable of being advanced and retracted with respect to the brake rotor, wherein the brake shoe is a component that is attached to the slide member. According to this structure, the brake shoe is not a member that is formed integrally on a component that is pressed by the elastic member, but rather, is a member that is attached to the slide member that is constituted as a separate element. Therefore, in case there is a design modification to the brake shoe, only the brake shoe needs to be modified while leaving the slide member intact, and thus design changes can easily be handled.

In the above-described brake mechanism, the second gear may extend in an arcuate shape conforming to the outer circumference of the brake rotor, and the brake shoe may be mounted on the slide member in a state of being capable of swinging slightly with respect to the slide member. According to such a structure, when the brake shoe abuts against the brake rotor, the angle of the brake shoe changes automatically to facilitate meshing of the first gear and the second gear over a predetermined range in the circumferential direction. Accordingly, the brake shoe is aligned and centered automatically with respect to the brake rotor, so that a suitable braking force can be exhibited.

In the above-described brake mechanism, the brake rotor, the brake shoe, and the slide member may be arranged inside a frame. On a wall of the frame that is formed on an opposite side from the brake rotor with the slide member interposed therebetween, an insertion hole may be disposed having a size that allows the elastic member to be inserted therethrough. Further, a retaining member that holds and presses the elastic member may be installed in the insertion hole. By such a structure, assembly and removal of the elastic member through the insertion hole can easily and swiftly be carried out.

In the above-described brake mechanism, the retaining member may be installed in the insertion hole so as to be capable of changing an amount of compression of the elastic member. According to this structure, by changing the depth at which the retaining member is installed with respect to the insertion hole, the amount of compression of the elastic member can be changed, and the force at which the brake shoe presses against the brake rotor can easily be adjusted. Moreover, if a screw-engagement structure is provided for installation of the retaining member with respect to the insertion hole, the position of the retaining member can easily be adjusted very finely.

Further, the present invention is characterized by a medical manipulator equipped with a distal end working unit on a distal end of a shaft that extends from a handle, and the distal end working unit being capable of being tilted with respect to the shaft, the medical manipulator being constituted so as to mechanically transmit an input operation with respect to a tilt operating member provided on the handle to thereby tiltably operate the distal end working unit, and further being equipped with a brake mechanism. The brake mechanism includes a brake rotor that rotates in conjunction with rotation of the tilt operating member, and a brake shoe, which is capable of advancing and retracting with respect to the brake rotor, and further is capable of contacting an outer circumference of the brake rotor. Based on an elastic force of an elastic member, the brake shoe is pressed against the brake rotor to thereby generate a braking force, and a braking action is released by separating the brake shoe away from the brake rotor in opposition to the elastic force. A first gear is disposed along a circumferential direction on the outer circumference of the brake rotor, and a second gear, which is capable of meshing with the first gear, is disposed on a portion of the brake shoe that confronts the outer circumference of the brake rotor. The brake rotor is a member that rotates in conjunction with rotation of the tilt operating member, and based on the elastic force of the elastic member, the brake shoe is pressed against the brake rotor, whereby rotation of the brake rotor is prevented, and an angle of the distal end working unit with respect to the shaft is fixed.

In accordance with the medical manipulator, even if the elastic force of the elastic member is small, a sufficient braking force can be obtained, and thus the operating force when braking is released in opposition to the elastic force of the elastic member can effectively be reduced.

In accordance with the brake mechanism of the present invention, it is possible to produce a large braking force while reducing an elastic force for pressing a brake shoe against a brake rotor. In accordance with the medical manipulator of the present invention, the operating force needed to release the braking action can be made smaller, thereby enhancing ease of operation.

DETAILED DESCRIPTION OF THE INVENTION

Hereinafter, preferred embodiments of a brake mechanism and a medical manipulator according to the present invention will be described in detail below with reference to the accompanying drawings.

Figure 1:
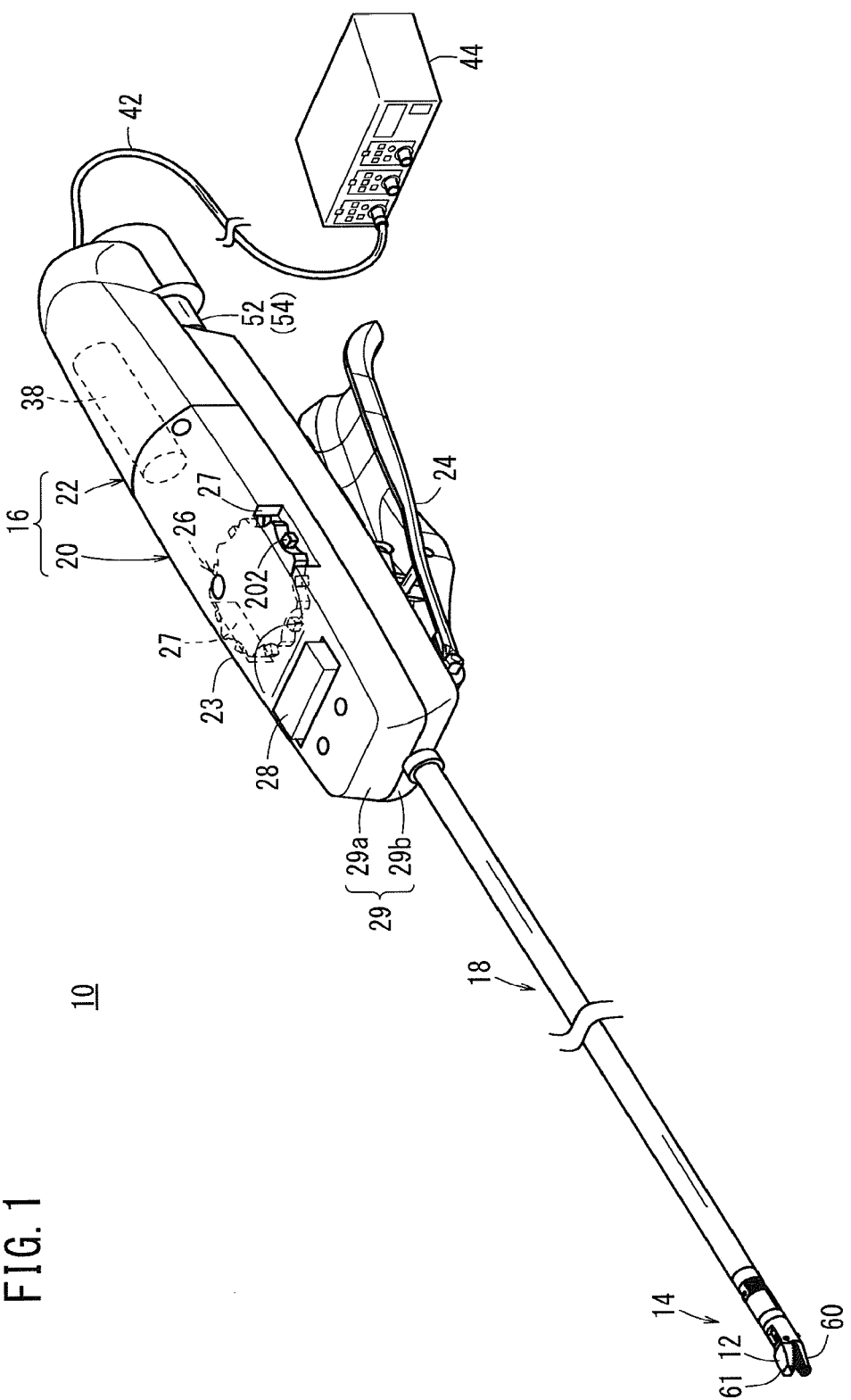
FIG. 1 is a perspective view with partial omission of a medical manipulator according to an embodiment of the present invention.

FIG. 1 is a perspective view with partial omission of a medical manipulator 10 (hereinafter referred to as a "manipulator 10") according to an embodiment of the present invention. The manipulator 10 is a medical device that grasps a needle, a suture thread, or a part of the living body or that touches the living body using a gripper 12 (end effector) provided at the distal end thereof, and carries out a predetermined treatment. The manipulator 10 is constituted as a needle driver that is capable of grasping a medical needle (a curved needle or the like) with the gripper 12 which is disposed on the distal end thereof.

The manipulator 10 is equipped with a distal end working unit 14 (working unit) including the gripper 12, a handle 16 that drives the gripper 12, and a shaft 18 that interconnects the gripper 12 and the handle 16. The gripper 12 is a portion that carries out a surgical treatment, and in the illustrated example, the gripper 12 includes first and second gripper members 60, 61, and is configured to carry out opening and closing operations on the basis of a predetermined opening and closing operation shaft.

The posture of the distal end working unit 14 including the gripper 12 can be changed at a plurality of degrees of freedom with respect to the shaft 18. In the present embodiment, the distal end working unit 14 can carry out a "tilting operation" (swinging operation) in which the distal end working unit 14 is operated to tilt in left and right directions with respect to an axis of the shaft 18, and a "rolling operation" in which the distal end working unit 14 is rotated about the axis in the longitudinal direction of the distal end working unit 14. Instead of swinging in left and right directions, the tilting operation may be an operation in which the distal end working unit 14 is operated in a tilting manner in upward and downward directions with respect to the axis of the shaft 18.

The shaft 18 is an elongated and small diameter tubular member. A plurality of members configured to make up a power transmission mechanism are inserted through and arranged in a hollow portion of the shaft 18. Such a power transmission mechanism transmits, from the handle 16 to the distal end working unit 14, power that is necessary for carrying out the opening and closing operation of the gripper 12, and the rolling operation and the tilting operation of the distal end working unit 14.

The handle 16 includes a handle main body 20 including a plurality of operating units, and a drive unit 22 including a motor 38, the drive unit 22 being capable of being attached to and detached from the handle main body 20. When the motor 38 is driven in a state in which the drive unit 22 is mounted on the handle main body 20, a driving force from the motor 38 is transmitted to the distal end working unit 14. Thus, the form of use thereof can be one in which, concerning a manipulator main body, which includes the handle main body 20, the shaft 18, and the distal end working unit 14, the manipulator main body can be discarded after being used a predetermined number of times, whereas the drive unit 22 can be used repeatedly many times by changing the manipulator main body that is connected to the drive unit 22.

The handle main body 20 comprises a body portion 23 that is connected to a proximal end of the shaft 18, a lever 24 constituting an opening and closing operating unit that is provided on the body portion 23, a tilt wheel 26 (operating member) constituting a tilt operating unit that is provided on the body portion 23, and a rolling switch 28 constituting a rolling operating unit that is provided on the body portion 23.

The body portion 23 makes up a part that is gripped by a user when the manipulator 10 is used. In the present embodiment, the body portion 23 is constituted in the form of a stick that extends over a certain length in the axial direction of the shaft 18. The body portion 23 includes a casing 29 made up from an upper cover 29a and a lower cover 29b, with drive components such as pulleys, gears, wires, etc., being arranged in the interior of the casing 29.

A lever 24 for performing an opening and closing operation of the gripper 12 is disposed on a lower part of the body portion 23, and is mounted swingably upward and downward about the distal end side thereof which serves as a support point. According to the present embodiment, the lever 24 is constructed as a manual operating element, in which an opening and closing operation of the gripper 12 is carried out by mechanically transmitting to the gripper 12 of the distal end working unit 14 an operating force applied with respect to the lever 24. More specifically, a structure is provided in which the gripper 12 is opened when the lever 24 is opened, and the gripper 12 is closed when the lever 24 is closed.

The tilt wheel 26 for carrying out a tilting operation of the distal end working unit 14 is disposed near the center in the longitudinal direction of the body portion 23. The tilt wheel 26 is constituted as a manual operating element, and the tilt wheel 26 is partially exposed from openings 27 provided on left and right sides of the casing 29. When the tilt wheel 26 is operated by being rotated, the operating force applied thereto is transmitted mechanically to the distal end working unit 14 through a tilting operation power transmission system, which is disposed internally in the handle 16 and the shaft 18, whereupon the distal end working unit 14 is tilted in a non-parallel direction (in left and right directions or upward and downward directions) with respect to the axis of the shaft 18.

The rolling switch 28 for carrying out a rolling operation of the distal end working unit 14 is disposed on an upper portion in the vicinity of the front end of the body portion 23. In the present embodiment, the rolling switch 28 is constituted as an electrical operating element, which supplies an operating command to the motor 38 through a controller 44.

When the rolling switch 28 is pressed, a signal corresponding to the pressed position is transmitted to the controller 44 through a connector 54 and a cable 42, and under the control of the controller 44, the motor 38 is driven and a driving force from the motor 38 is transmitted to the distal end working unit 14, whereby the distal end working unit 14 is rotated about the longitudinal axis of the distal end working unit 14. In the present embodiment, the distal end working unit 14 is rotated clockwise when a right-hand part of the rolling switch 28 is pressed, and the distal end working unit 14 is rotated counterclockwise when a left-hand part of the rolling switch 28 is pressed.

Figure 2:
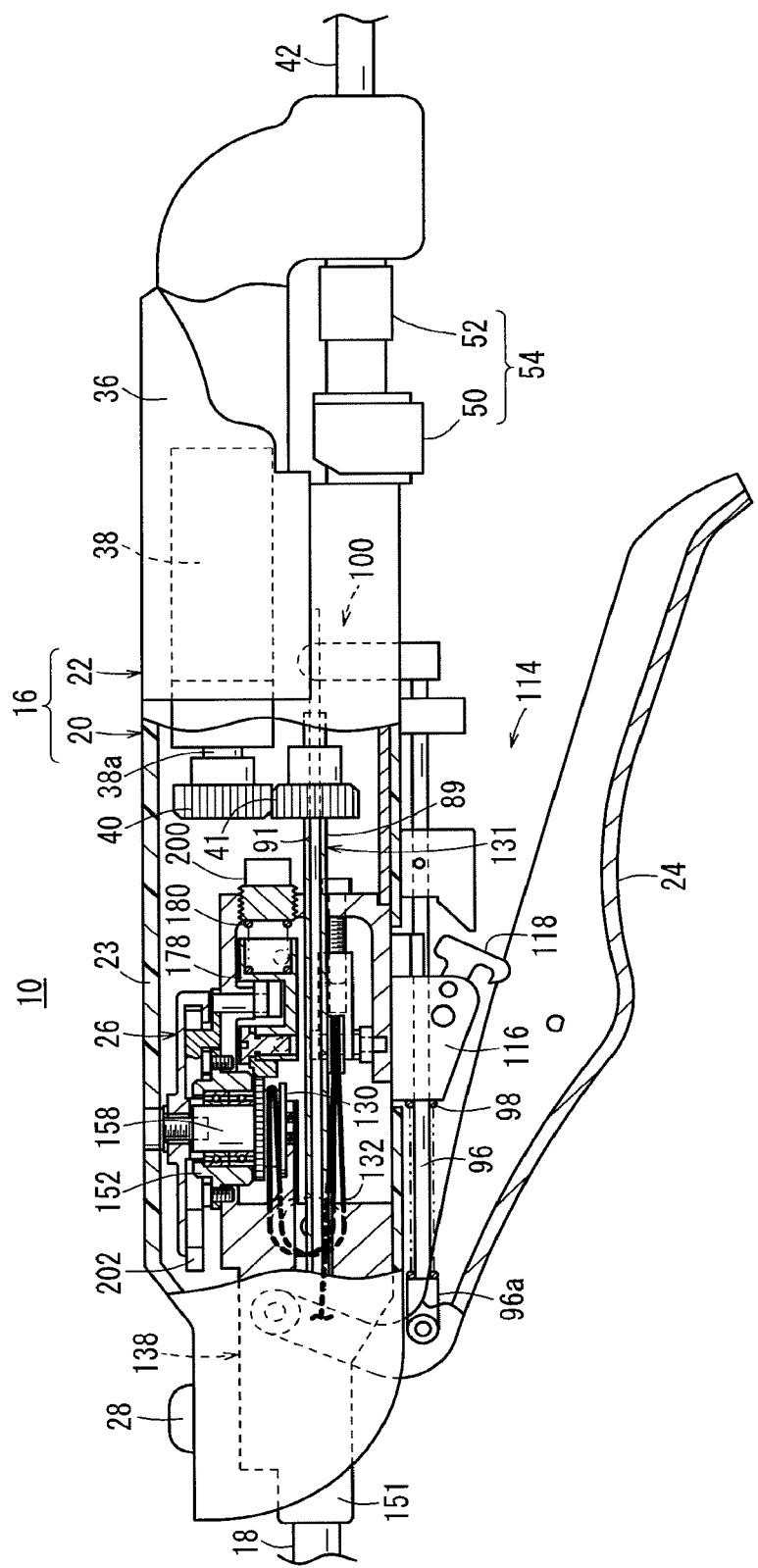
FIG. 2 is a side view partially shown in cross section of the medical manipulator illustrated in FIG. 1.

FIG. 2 is a side view partially shown in cross section of the handle 16 of the manipulator 10. As shown in FIG. 2, the drive unit 22 includes a housing 36, the motor 38 (drive source) arranged in the interior of the housing 36, and a drive gear 40 (pinion gear), which is fixed to an output shaft of the motor 38. The drive unit 22 is detachably attached to the rear of the handle main body 20.

The drive unit 22 is connected to the controller 44 through the cable 42 that includes a power line and a signal line. The controller 44 controls the supply of power and driving of the motor 38, and receives electrical power from an external power source. When the rolling switch 28 is operated, a signal corresponding to the operation thereof is transmitted to the controller 44, and the controller 44 controls driving of the motor 38.

Upon attachment of the drive unit 22 to the body portion 23 of the handle main body 20, the drive gear 40, which is fixed to the output shaft 38a of the motor 38, is brought into meshing engagement with a driven gear 41 that is disposed inside the body portion 23. In this condition, when the motor 38 is rotated, the rotary driving force of the motor 38 is transmitted to the side of the handle main body 20 through the drive gear 40 and the driven gear 41.

As shown in FIG. 2, a handle side connector 50 is disposed on the rear of the body portion 23 of the handle main body 20, and a unit side connector 52 is disposed on the rear of the drive unit 22. If the rolling switch 28 is operated in a condition in which the handle side connector 50 and the unit side connector 52 are connected, a signal corresponding to the state of the rolling switch 28 is transmitted to the controller 44 through the connector 54 and the signal line of the cable 42, and under the control of the controller 44, the motor 38 that is mounted in the drive unit 22 is driven.

In the manipulator 10 according to the present embodiment, only the rolling operation of the distal end working unit 14 is effected by an electrical drive provided through the motor 38, whereas the tilting operation and the opening/closing operation of the distal end working unit 14 are effected by a manual drive. However, in a modification of the manipulator 10, a structure may be provided in which not only the rolling operation, but also one or both of the tilting operation and the opening/closing operation are effected by an electrical drive.

Figure 3:
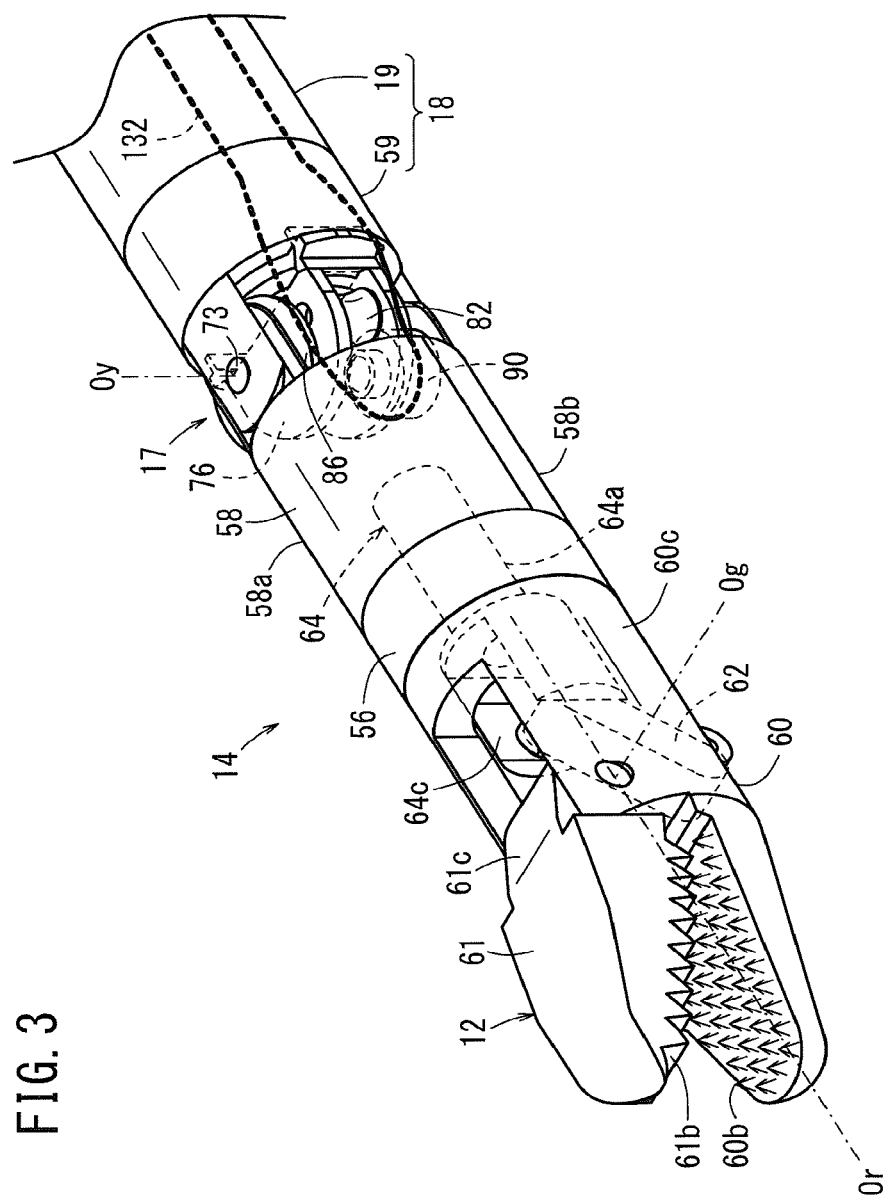
FIG. 3 is a perspective view of a distal end working unit of the medical manipulator illustrated in FIG. 1.
Figure 4:
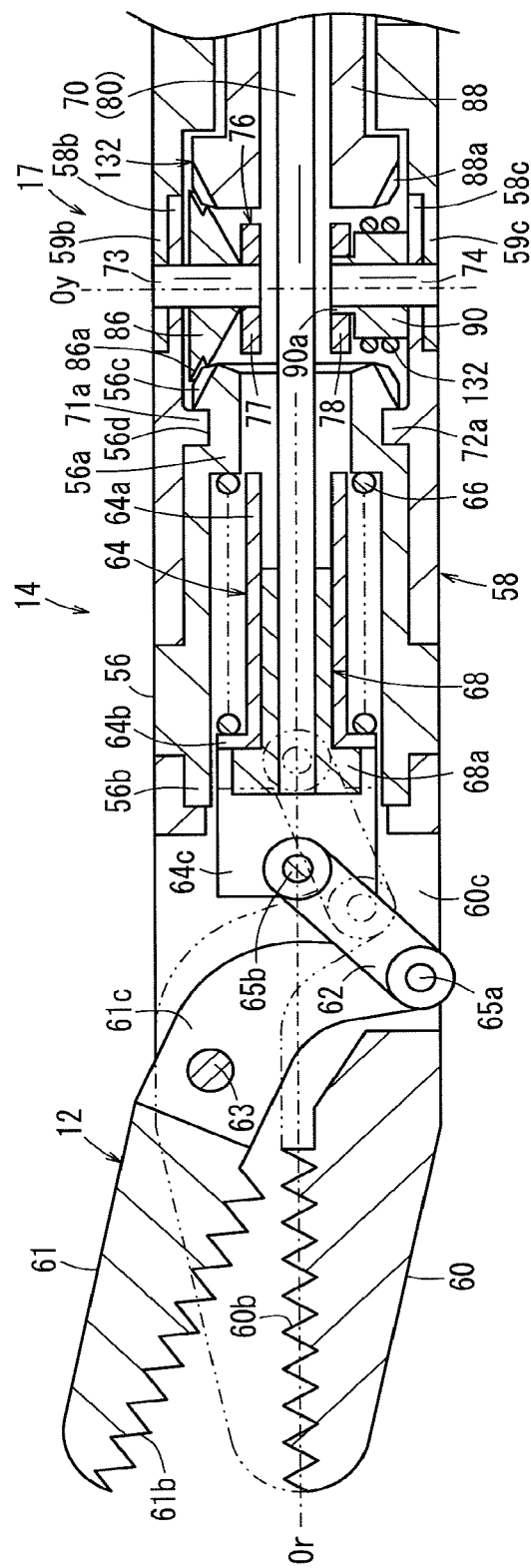
FIG. 4 is a vertical cross-sectional view of the distal end working unit.

FIG. 3 is a perspective view showing the distal end working unit 14 which is connected to the distal end of the shaft 18. FIG. 4 is a vertical cross-sectional view of the distal end working unit 14. As shown in FIGS. 3 and 4, the distal end working unit 14 includes the gripper 12 that is capable of being opened and closed, a rotating sleeve 56 of a hollow cylindrical shape, to which the gripper 12 is fixed, and a distal end side fulcrum block 58 that is capable of rotatably supporting the rotating sleeve 56 in an axially rotatable manner at an inner circumferential portion thereof.

The gripper 12 is made up from a first gripper member 60 and a second gripper member 61. The first gripper member 60 and the second gripper member 61 are connected by a pin 63 so as to be capable of rotating about a gripper axis Og. An object to be gripped, for example, a needle or the like, is gripped by the first gripper member 60 and the second gripper member 61.

The second gripper member 61 is connected through a pin 65*a*, a link member 62, and a pin 65*b* to a transmission member 64. The transmission member 64 includes a guide tube 64*a*, a flange 64*b* disposed on a distal end of the guide tube 64*a*, and support arms 64*c* that extend mutually in parallel in the direction of the distal end from edges of the flange 64*b*. The transmission member 64 is arranged so as to be movable in the axial direction in the interior of the rotating sleeve 56.

A compression spring 66 is arranged between the transmission member 64 and the rotating sleeve 56. One end of the compression spring 66 abuts against the flange 64*b* of the transmission member 64, whereas the other end thereof abuts against a stepped part 56*a* provided on an inner circumferential portion of the rotating sleeve 56, so that the transmission member 64 normally is elastically biased in the direction of the distal end.

An end collar 68 is inserted into the transmission member 64 from the distal end side. A distal end of the end collar 68 is constituted as an engaging bulge 68*a* that comes into abutment and engages with a distal end surface of the guide tube 64*a* of the transmission member 64. The end collar 68 is fixed to a distal end of a pull wire 70 that passes through a joint 17 between the distal end working unit 14 and the shaft 18.

The pull wire 70 forms a member that moves in an advancing and retracting manner in the interior of the shaft 18 and the interior of the distal end working unit 14 responsive to an operation made with respect to the lever 24 of the handle 16. The joint 17 that is present between the distal end working unit 14 and the shaft 18 includes a pair of joint pins 73, 74, which are arranged on the tilt axis Oy. In addition, the pull wire 70, which constitutes part of the opening and closing drive transmission member 80, is capable of advancing and retracting in a direction intersecting the axial direction of the joint pins 73, 74, through a gap provided between the pair of joint pins 73, 74.

When the pull wire 70 is displaced in the direction of the proximal end, the transmission member 64 is pushed toward the proximal end by the end collar 68 that is fixed to the pull wire 70, whereby the transmission member 64 is displaced in the direction of the proximal end in opposition to the biasing force of the compression spring 66. Accompanying displacement of the transmission member 64 toward the proximal end, the second gripper member 61, which is connected to the link member 62, is rotated in a closing direction with respect to the first gripper member 60. In FIG. 4, the second gripper member 61 is shown by an imaginary line, in a state of being closed to a position at which the gripping face 61*b* of the second gripper member 61 and the gripping face 60*b* of the first gripper member 60 are placed in contact.

From the state of being closed to the position at which the gripping face 61*b* of the second gripper member 61 and the gripping face 60*b* of the first gripper member 60 are in contact, when the pull wire 70 and the end collar 68 are advanced, since the transmission member 64 is urged forward by the elastic force of the compression spring 66, the first gripper member 60 rotates through the link member 62 in a direction to open with respect to the second gripper member 61, and is restored to its original state. This operation is referred to as an opening and closing operation of the gripper 12.

In the present embodiment, although concerning the gripper 12, a case has been described in which the first gripper member 60 is constituted as a fixed member and the second gripper member 61 is constituted as a movable member, both of the gripper members may be constituted as movable members.

A distal end part of a pull rod 91 shown in FIG. 2 is connected to the proximal end of the pull wire 70. The pull rod 91 is a tubular member and is arranged by insertion thereof into the interior of the shaft 18. The pull wire 70 and the pull rod 91 are capable of relative rotation around a common axis, and are connected in the interior of the shaft 18 so as to be capable of transmitting a tensile force in the direction of the proximal end of the pull rod 91 to the pull wire 70.

Due to being constructed in this manner, when the pull rod 91 is displaced in the axial direction, the pull wire 70, which is connected to the pull rod 91, also is displaced in the axial direction to thereby carry out the opening and closing operation of the gripper 12. Further, when the distal end working unit 14 implements the rolling operation, since the pull wire 70 can be rotated with respect to the pull rod 91, the rolling operation of the distal end working unit 14 is not hindered.

As shown in FIG. 2, the pull rod 91 is inserted through the interior of a hollow shaft 89, and the proximal end thereof projects outwardly from the proximal end of the hollow shaft 89. On the other hand, at a distal end part thereof, the lever 24 is connected so as to be capable of swinging with respect to the body portion 23, at a location near the distal end of the body portion 23. A distal end of a lever rod 96, which is arranged downwardly of the body portion 23 substantially in parallel with the longitudinal direction of the body portion 23, is connected rotatably near the distal end of the lever 24.

A hook holder 116 that supports a hook member 118 is fixed to a lower part of the body portion 23. A compression spring 98 is arranged between a distal end surface of the hook holder 116 and a distal end expanded diameter portion 96a of the lever rod 96. The compression spring 98 normally applies a biasing force to the lever rod 96 in the distal end direction. Consequently, by the elastic force of the compression spring 98, the lever 24, which is connected to the lever rod 96, normally receives a force in a direction to open with respect to the body portion 23. A driving force from the lever 24 is transmitted through an intermediate transmission mechanism 100 to the pull rod 91 and the pull wire 70, which constitute the opening and closing drive transmission member 80.

In the handle main body 20, a condition in which the lever 24 is open with respect to the body portion 23 (see FIG. 2) is regarded as an initial position. In the initial position, the pull rod 91 is advanced to a position at which the gripper 12 is in a fully open state. When the user grips the lever 24, and pulls the lever 24 toward the body portion 23 (thereby closing the lever 24), the lever rod 96 is displaced in the direction of the proximal end. At this time, since the pull rod 91 is pulled in the direction of the proximal end through the intermediate transmission mechanism 100, the gripper 12 is operated in a direction to close.

Next, a mechanism related to the rolling operation of the distal end working unit 14 will be described. As shown in FIG. 4, the distal end of the rotating sleeve 56 is fitted and fixedly attached to the base portion 60c of the first gripper member 60. A bevel gear part 56c is disposed on a proximal end of the rotating sleeve 56. The gripper 12, the rotating sleeve 56, the transmission member 64, the end collar 68, and the compression spring 66 are capable of integrally rotating relative to the distal end side fulcrum block 58 about the longitudinally directed roll axis Or of the distal end working unit 14.

The distal end side fulcrum block 58, which is of a hollow cylindrical shape, is capable of being changed in posture with respect to the axial direction of the shaft 18, and rotatably supports the rotating sleeve 56 on an inner circumferential portion thereof. By engagement between circumferentially extending projections 71a, 72a, which are provided on the inner circumference of the distal end side fulcrum block 58, and an annular recess 56d that is provided on the rotating sleeve 56, the rotating sleeve 56 is connected to the distal end side fulcrum block 58 such that the rotating sleeve 56 is rotatable relative to the distal end side fulcrum block 58, but immovable in the axial direction with respect to the distal end side fulcrum block 58.

The distal end side fulcrum block 58 and a shaft side fulcrum block 59 are connected together rotatably about the tilt axis Oy by joint pins 73, 74. The joint pins 73, 74 are fitted into tongue pieces 58b, 58c disposed on upper and lower parts on the proximal end of the distal end side fulcrum block 58, and into tongue pieces 59b, 59c disposed on upper and lower parts on the distal end of the shaft side fulcrum block 59. The shaft side fulcrum block 59 is fixed to the distal end of a hollow shaft main body 19 that constitutes the body portion of the shaft 18 (see FIG. 3). The shaft 18 is constituted from the shaft side fulcrum block 59 and the shaft main body 19. The tilt axis Oy is set in the vertical direction. However, the tilt axis Oy may be set in a different direction that intersects the axis of the shaft main body 19.

As shown in FIG. 4, a bevel gear 86 is supported rotatably by one of the joint pins 73. The teeth 86a of the bevel gear 86 are enmeshed with the bevel gear part 56c provided on the proximal end of the rotating sleeve 56, and with a bevel gear part 88a that is provided on the distal end of a gear member 88. The gear member 88 is a hollow cylindrical member, with the pull wire 70 being inserted through a hollow interior portion thereof.

Upon rotation of the gear member 88, the rotational force of the gear member 88 is transmitted to the rotating sleeve 56 through the bevel gear 86 and the bevel gear part 56c, and the rotating sleeve 56 together with the gripper 12 that is fixed thereto are rotated about the roll axis Or with respect to the distal end side fulcrum block 58. This operation is referred to as a rolling operation of the distal end working unit 14.

In the present embodiment, the rolling operation of the distal end working unit 14 is carried out by transmitting a driving force of the motor 38 through a rolling drive transmission system to the distal end working unit 14. The rolling drive transmission system includes, as shown in FIG. 2, the motor 38, the drive gear 40 that is fixed to the output shaft 38a of the motor 38, the driven gear 41 that is enmeshed with the drive gear 40, and the hollow shaft 89 to which the driven gear 41 is fixed. The rolling drive transmission system further includes, as shown in FIG. 4, the gear member 88 that is fixed to the distal end of the hollow shaft 89, the bevel gear 86 that is enmeshed with the gear member 88, and the rotating sleeve 56 that is enmeshed with the bevel gear 86.

In the present embodiment, a rolling drive transmission pipe 131 is constituted by the gear member 88 and the hollow shaft 89. Further, a rotating drive transmission unit, which transmits the rotary driving force from the handle 16 to the distal end working unit 14, is constituted from the rolling drive transmission pipe 131, the bevel gear 86, and the rotating sleeve 56.

In a state in which the drive unit 22 is mounted on the handle main body 20, and the controller 44 is connected to a power source, when the rolling switch 28 shown in FIG. 1 is operated by pressing, the motor 38 rotates, and a driving force from the motor 38 is transmitted to the distal end working unit 14 through the drive gear 40, the driven gear 41, the rolling drive transmission pipe 131 (the hollow shaft 89 and the gear member 88), the bevel gear 86, and the rotating sleeve 56. As a result, a rolling operation of the distal end working unit 14 is carried out. In this manner, with the manipulator 10, transmission of the rotational force from the handle 16 to the distal end working unit 14 is carried out through the rolling drive transmission pipe 131, etc. Therefore, the distal end working unit 14 can be operated to roll over an unlimited range of rotation.

Since the portion (the pull wire 70) of the opening and closing drive transmission member 80 (the pull wire 70 and the pull rod 91) corresponding to the joint 17 is flexible, with a simple structure, the opening and closing driving force can be transmitted appropriately to the gripper 12. Accordingly, without increasing the complexity of the mechanism of the distal end working unit 14, a structure can be maintained that enables the opening and closing operation as well as the tilting operation of the distal end working unit 14, while also realizing a rolling operation having an unlimited range of rotation.

Next, a mechanism related to the tilting operation of the distal end working unit 14 will be described. As shown in FIG. 4, a driven pulley 90 is supported rotatably by the other joint pin 74. The driven pulley 90 is fixed to an inner surface of the tongue piece 58c of the distal end side fulcrum block 58. Accordingly, when a drive pulley 130 is rotated, the driven pulley 90 and the distal end side fulcrum block 58 are capable of integrally rotating relative to the shaft side fulcrum block 59. A tilting operation wire 132 is trained around the driven pulley 90. A portion of the wire 132 is fixed to the driven pulley 90, and the wire 132 passes through the interior of the shaft 18 up to the handle 16.

When the driven pulley 90 is driven and rotated by the wire 132, the distal end side fulcrum block 58, which is fixed to the driven pulley 90, is rotated integrally with the driven pulley 90. As a result, the distal end working unit 14 including the distal end side fulcrum block 58, the rotating sleeve 56, and the gripper 12 is rotated about the tilt axis Oy with respect to the shaft 18. This operation is referred to as a tilting operation of the distal end working unit 14. Assuming the condition in which the distal end working unit 14 is oriented in a straight manner with respect to the shaft 18 to be a neutral position (reference position), the tilting operation of the distal end working unit 14 includes a movement range to a plus side (right side) and to a minus side (left side), respectively.

As shown in FIG. 2, the drive pulley 130, which rotates in conjunction with rotation of the tilt wheel 26, is disposed in the interior of the handle main body 20. A tilting operation wire 132 is trained around the drive pulley 130. An annular space, which extends along the axis of the shaft 18, is provided between the inner circumference of the shaft 18 and the outer circumference of the rolling drive transmission pipe 131. The wire 132 passes through the interior of the annular space, and is trained around the driven pulley 90 (see FIG. 4) at the distal end side of the shaft 18.

The tilt wheel 26 shown in FIGS. 1 and 2 is rotated by manual operation, and the operating force applied to the tilt wheel 26 is then transmitted to the wire 132 that is trained around the drive pulley 130, thereby driving the wire 132. Driving of the wire 132 is output at the distal end of the shaft 18 to rotate the driven pulley 90, whereby the tilting operation of the distal end working unit 14 with respect to the shaft 18 is carried out.

The manipulator 10 is further equipped with a brake mechanism 134, which restricts movement of the power transmission mechanism between the tilt wheel 26 and the distal end working unit 14, and a brake release mechanism 136 to release the braking action performed by the brake mechanism 134.

Figure 5:
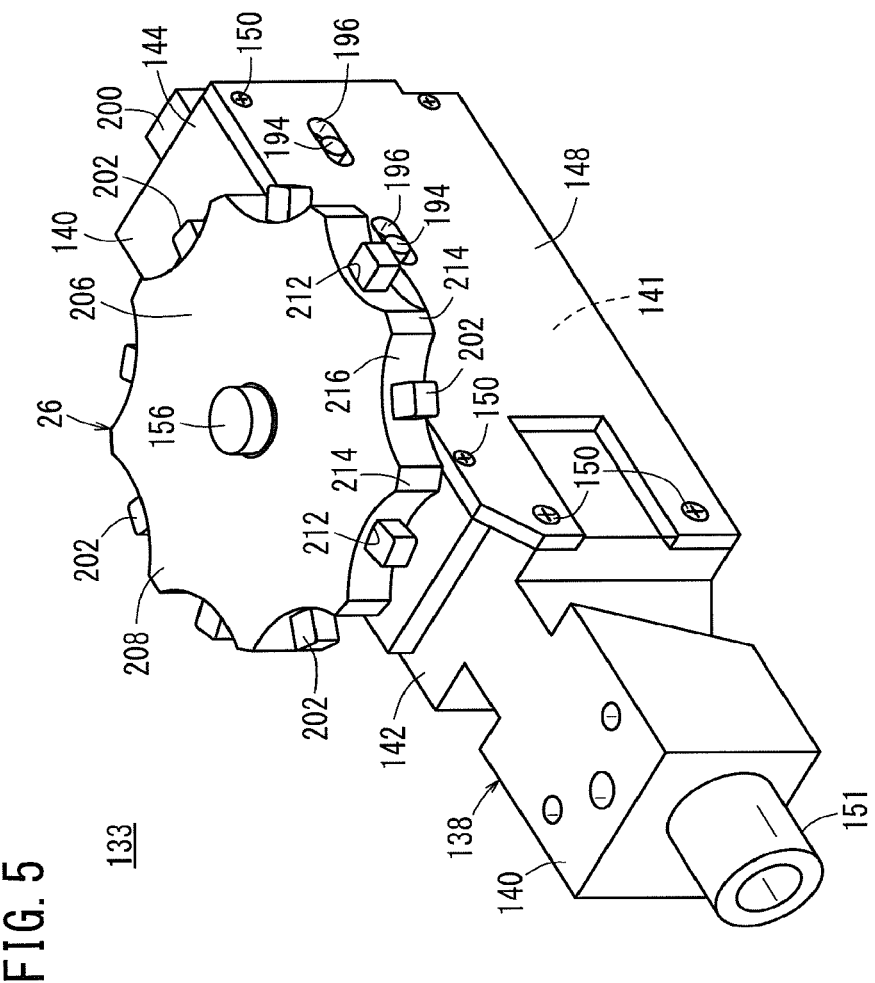
FIG. 5 is a perspective view of a mechanism unit.
Figure 6:
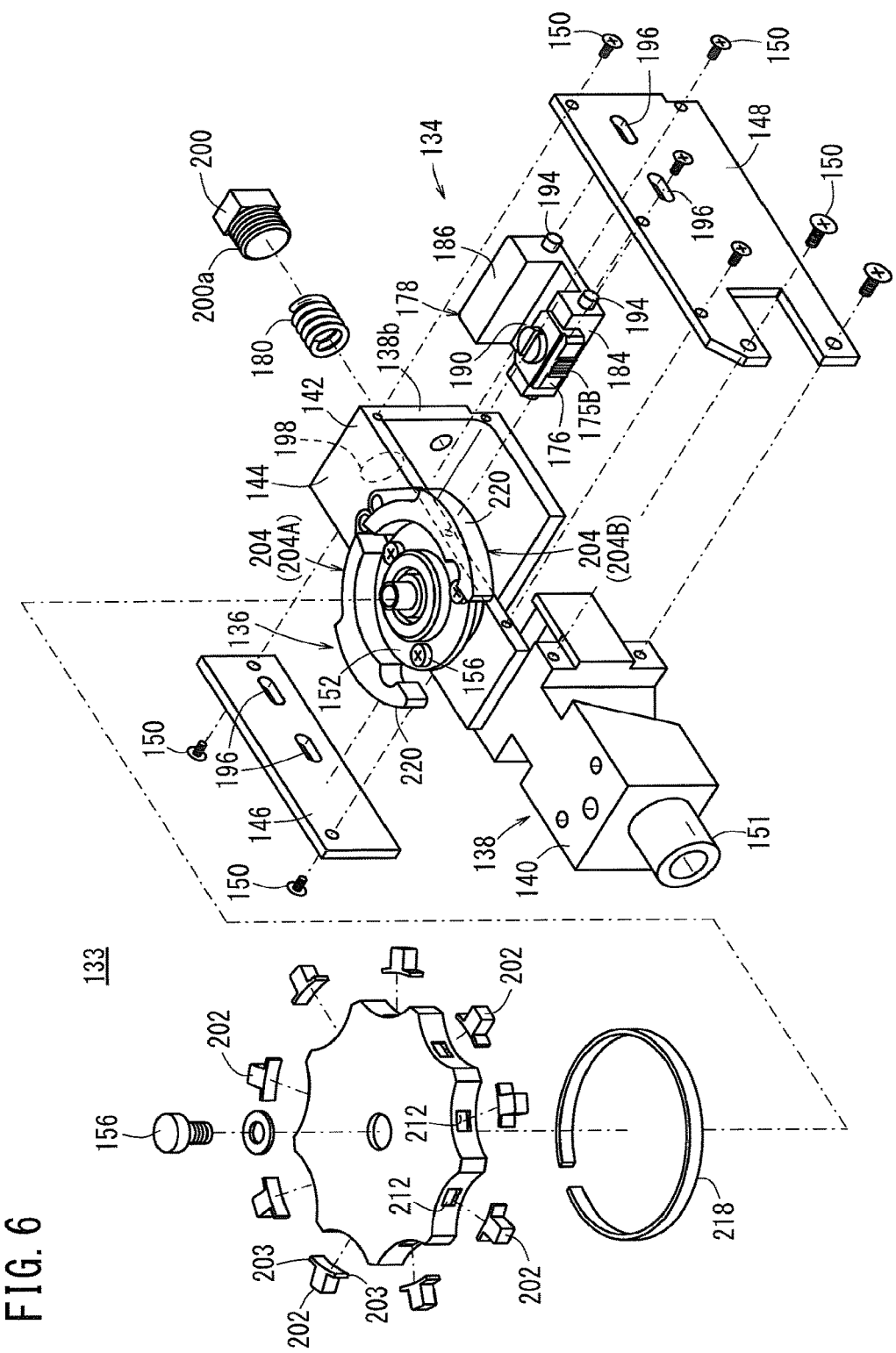
FIG. 6 is an exploded perspective view of the mechanism unit.
Figure 7:
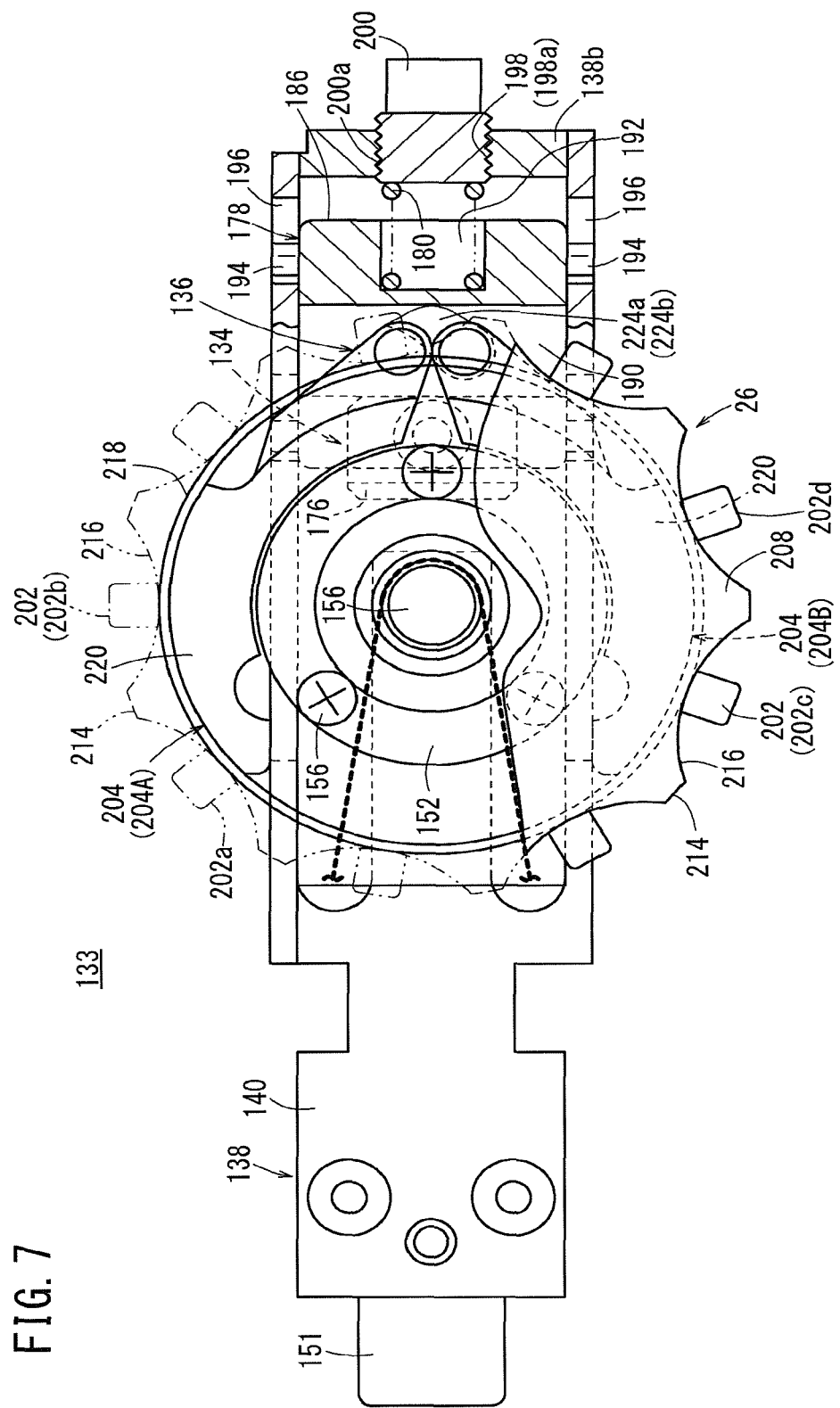
FIG. 7 is a plan view partially shown in cross section of the mechanism unit.
Figure 8:
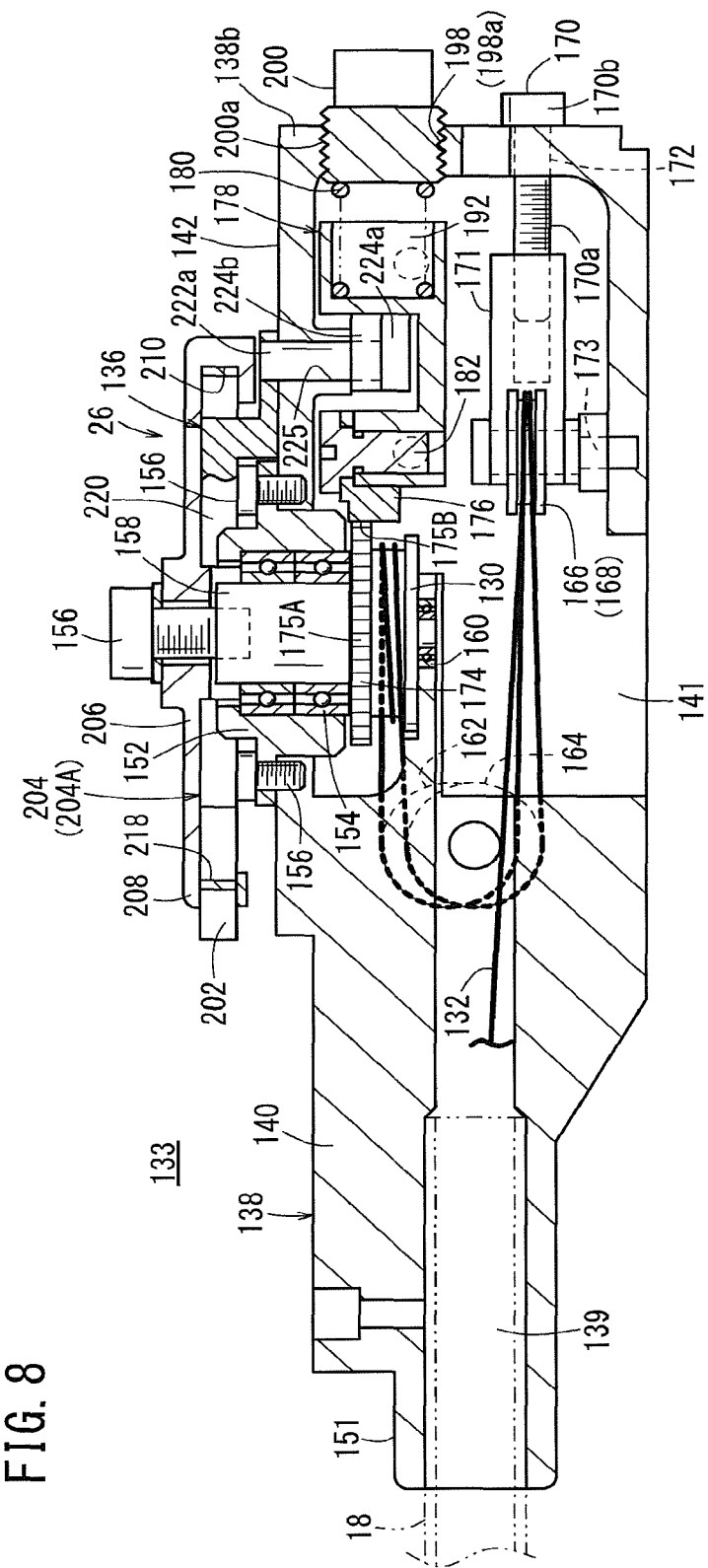
FIG. 8 is a vertical cross-sectional view of the mechanism unit.

FIG. 5 is a perspective view of a mechanism unit 133, which is disposed in the handle main body 20. FIG. 6 is an exploded perspective view of the mechanism unit 133. FIG. 7 is a plan view partially shown in cross section of the mechanism unit 133. FIG. 8 is a vertical cross-sectional view of the mechanism unit 133. The mechanism unit 133 includes a frame 138, the tilt wheel 26 that is attached rotatably to the frame 138, the brake mechanism 134 that is incorporated in the frame 138, and the brake release mechanism 136 that is incorporated in the frame 138.

Substantially all except for a portion of the mechanism unit 133 is arranged in the interior of the handle main body 20. The frame 138 is a hollow structure comprising a distal end side structural part 140 including a through hole 139 that penetrates forwardly and rearwardly, and a mechanism box part 142 disposed rearwardly of the distal end side structural part 140, including an interior space 141 that communicates with the through hole 139. The shaft 18 is inserted into and fixed to the distal end side of the frame 138. The frame 138 includes a frame main body 144 comprising the distal end side structural part 140, and an upper wall, a rear wall, and a bottom wall of the mechanism box part 142, a right side wall plate 146 comprising a right side wall of the mechanism box part 142, and a left side wall plate 148 comprising a left side wall of the mechanism box part 142. The right side wall plate 146 and the left side wall plate 148 are fixed to the frame main body 144 by suitable fixing means (e.g., screws 150). A cylindrical projecting part 151, which is disposed on the distal end of the frame 138, projects out from the distal end of the casing 29.

As shown in FIG. 8, a bearing 154 is arranged through a bearing housing 152 on an upper portion of the frame 138. The bearing housing 152 is fixed to the frame 138 by suitable means (e.g., screws 156), and the bearing 154 is mounted on an inner side of the bearing housing 152. A wheel shaft 158, which is fixed by a screw 156 to the tilt wheel 26, is supported by the bearing 154. By such a structure, the tilt wheel 26 is supported rotatably with respect to the frame 138.

With the present embodiment, the tilt wheel 26 can be rotated about a vertically directed axis of the manipulator 10. Further, with the present embodiment, since the drive pulley 130 is connected through the wheel shaft 158 coaxially with the tilt wheel 26, the tilt wheel 26 and the drive pulley 130 are rotated together in unison.

As shown in FIG. 8, an end of the wheel shaft 158 on the opposite side of the other end to which the tilt wheel 26 is fixed, is supported by another bearing 160 disposed in the frame 138. On the wheel shaft 158, below a location thereof where the wheel shaft 158 is supported by the bearing 154, the drive pulley 130 is disposed, around which the aforementioned wire 132 is trained. The drive pulley 130 is arranged between the bearing 154 and the bearing 160.

As shown in FIG. 8, the wire 132 is trained around a first intermediate pulley 162 and a second intermediate pulley 164, which are arranged forwardly of the drive pulley 130, and around a first tension pulley 166 and a second tension pulley 168, which are arranged rearwardly of the drive pulley 130.

The first intermediate pulley 162 and the second intermediate pulley 164 are supported rotatably on the frame 138 at a position in front of the drive pulley 130, so as to be rotatable about an axis oriented perpendicularly (in a lateral direction of the manipulator 10) with respect to the rotational axis of the drive pulley 130. The first intermediate pulley 162 and the second intermediate pulley 164 are juxtaposed in a direction perpendicular to the rotational axis of the drive pulley 130, and are disposed mutually at different heights.

In the present embodiment, the first tension pulley 166 and the second tension pulley 168 are arranged at positions separated from one another laterally (in a direction perpendicular to the sheet of FIG. 8), and are supported rotatably about axes that are parallel with the rotational axis of the drive pulley 130 (in a vertical direction of the manipulator 10). More specifically, the first tension pulley 166 is supported by a pulley shaft 173 rotatably at a distal end of a pulley holder 171. The second tension pulley 168 also is supported in the same manner as the first tension pulley 166.

Two adjustment bolts 170 are provided, corresponding respectively to the first tension pulley 166 and the second tension pulley 168. A threaded rod 170*a* of each adjustment bolt 170 is inserted from the rear in a through hole 172 that is provided in a rear wall 138*b* of the frame 138, and a head 170*b* of the adjustment bolt 170 abuts against the rear wall 138*b*. When the adjustment bolt 170 is rotated, the pulley holder 171 is moved in forward and rearward directions by a screwing action thereof.

Accordingly, by operating one of the adjustment bolts 170, the first tension pulley 166 that is supported by the one of the pulley holders 171 is positionally adjusted, and the tensile force that is applied to the one side portion of the wire 132 between the drive pulley 130 and the driven pulley 90 can be adjusted. Further, by operating the other of the adjustment bolts 170, the second tension pulley 168 that is supported by the other of the pulley holders 171 is positionally adjusted, and the tensile force that is applied to the other side portion of the wire 132 between the drive pulley 130 and the driven pulley 90 can be adjusted.

Next, the structure of the brake mechanism 134 will be described. The brake mechanism 134 includes a brake rotor 174, which rotates in conjunction with rotation of the tilt wheel 26, a brake shoe 176 that is capable of contacting an outer peripheral part of the brake rotor 174, a slide member 178 to which the brake shoe 176 is attached, and an elastic member 180 that elastically biases or urges the slide member 178.

In the present embodiment, the brake rotor 174 is disposed on a power transmission path between the tilt wheel 26 and the distal end working unit 14, and more specifically, as shown in FIG. 8, is disposed on the wheel shaft 158 adjacent to the drive pulley 130. The brake rotor 174 is shaped in the form of a disk, having a first gear 175A provided on an outer circumferential part thereof along a circumferential direction thereof.

Figure 9:
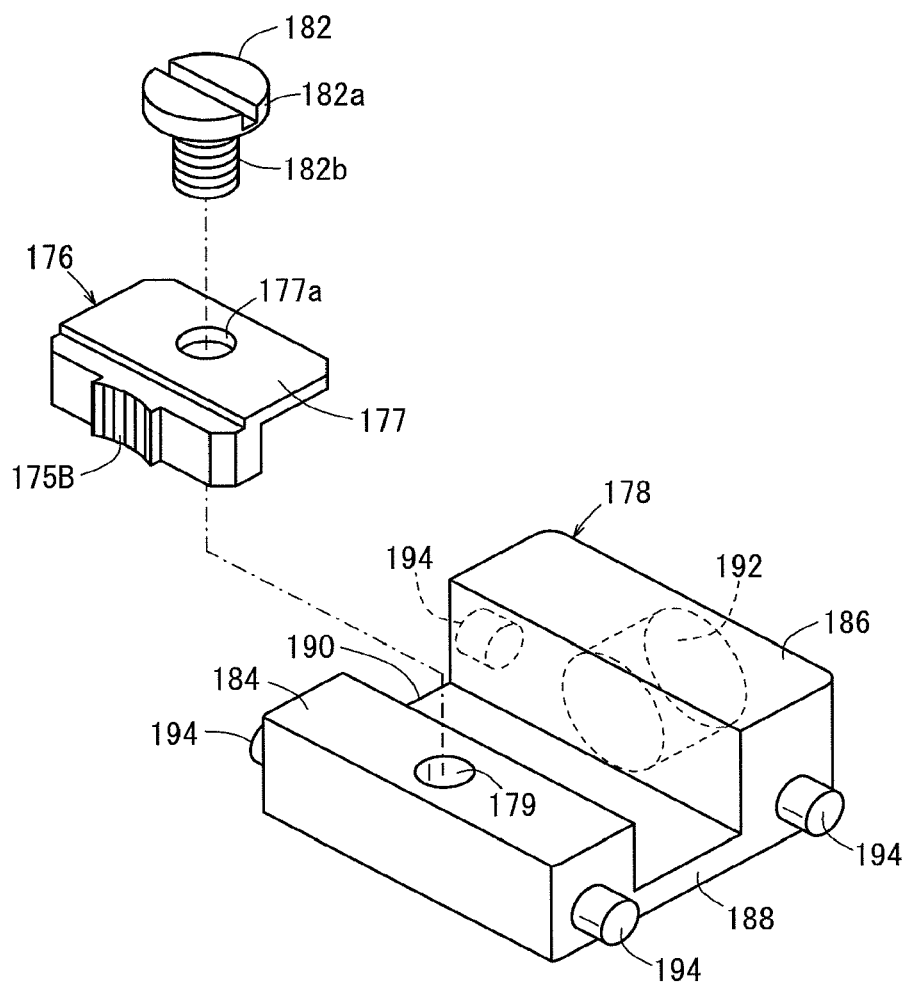
FIG. 9 is an exploded perspective view of a slide member, a brake shoe, and a bolt.

The brake shoe 176 is capable of being advanced and retracted with respect to the brake rotor 174. A second gear 175B, which can be enmeshed with the first gear 175A, is disposed on a portion of the brake shoe 176 that confronts the outer circumferential part of the brake rotor 174. As shown in FIG. 9, the second gear 175B extends in an arcuate shape that conforms to the outer circumferential part of the brake rotor 174. The brake shoe 176 is a component that is formed in an L-shape in the illustrated example, and is attached to the slide member 178 by a fixing means (a bolt 182 in the illustrated example).

Figure 10:
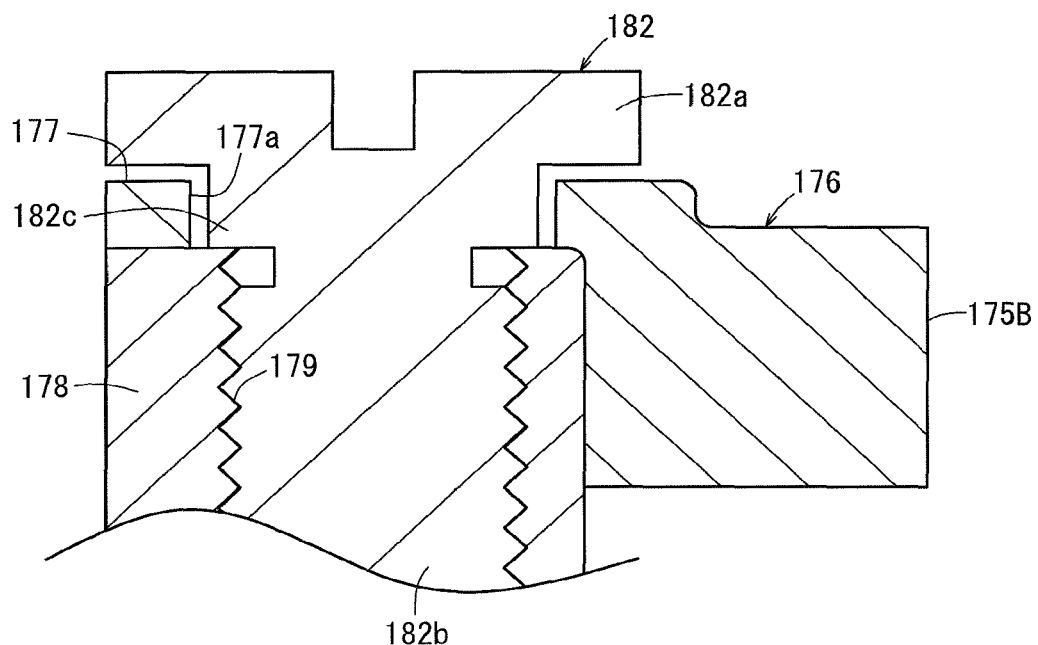
FIG. 10 is a cross-sectional view with partial omission of the slide member, the brake shoe, and the bolt.

As shown in FIG. 10, the bolt 182 includes a head 182a, a threaded rod 182b on which male threads are formed, and an intermediate part 182c formed between the head 182a and the threaded rod 182b. The threaded rod 182b is screw-engaged in a screw hole 179 provided in the slide member 178. The outer diameter of the intermediate part 182c is less than the outer diameter of the head 182a and greater than the outer diameter of the threaded rod 182b. The intermediate part 182c is arranged in a hole 177a provided in a mounting plate 177 of the brake shoe 176. The mounting plate 177 is disposed between the slide member 178 and the head 182a of the bolt 182.

The outer diameter of the intermediate part 182c is slightly smaller than the inner diameter of the hole 177a provided in the mounting plate 177, and the thickness in the axial direction of the intermediate part 182c is slightly thicker than that of the mounting plate 177. Therefore, gaps are provided, respectively, between the outer circumferential surface of the intermediate part 182c and the inner wall surface that makes up the hole 177a, and between the upper surface of the mounting plate 177 and the lower surface of the head 182a. In this manner, the brake shoe 176 is mounted with a certain amount of play with respect to the slide member 178. Stated otherwise, the brake shoe 176 is mounted on the slide member 178 in a swingable condition, which enables a slight amount of swinging about the axis of the bolt 182 with respect to the slide member 178.

As shown in FIG. 8, the slide member 178 is capable of being advanced and retracted with respect to the brake rotor 174, and normally is elastically pressed by the elastic member 180 toward the brake rotor 174.

As shown in FIG. 9, the slide member 178 includes a front part 184 constituting a front side thereof, a rear part 186 constituting a rear side thereof, and an intermediate structural part 188 that connects a lower part of the front part 184 with a lower part of the rear part 186. A groove 190 that extends in a widthwise direction of the slide member 178 is formed by a rear surface of the front part 184, a front surface of the rear part 186, and an upper surface of the intermediate structural part 188. An insertion hole 192, which opens rearwardly, is formed centrally in the widthwise direction of the rear part 186. One end side of the elastic member 180 is inserted in the insertion hole 192.

Further, on both left and right side surfaces of the slide member 178, pins 194 are formed that project out respectively at front and back spaced positions. The pins 194 are inserted slidably in forward and rearward directions in long holes 196 that are formed and extend longitudinally in the right side wall plate 146 and the left side wall plate 148 of the frame 138. By such a structure, the slide member 178 is capable of being advanced and retracted with respect to the brake rotor 174 integrally with the brake shoe 176 inside the frame 138.

In the present embodiment, the elastic member 180 is constituted from a coil spring. Instead of a coil spring, another form of spring (e.g., a plate spring, a torsion spring, etc.) or a rubber body may be used. In the frame 138, on a rear wall 138b, which is formed on an opposite side from the brake rotor 174 with the slide member 178 interposed therebetween, an insertion hole 198 is disposed having a size that allows the elastic member 180 to be inserted therethrough. A retaining member 200 that holds and presses the elastic member 180 is installed in the insertion hole 198.

Figure 11:
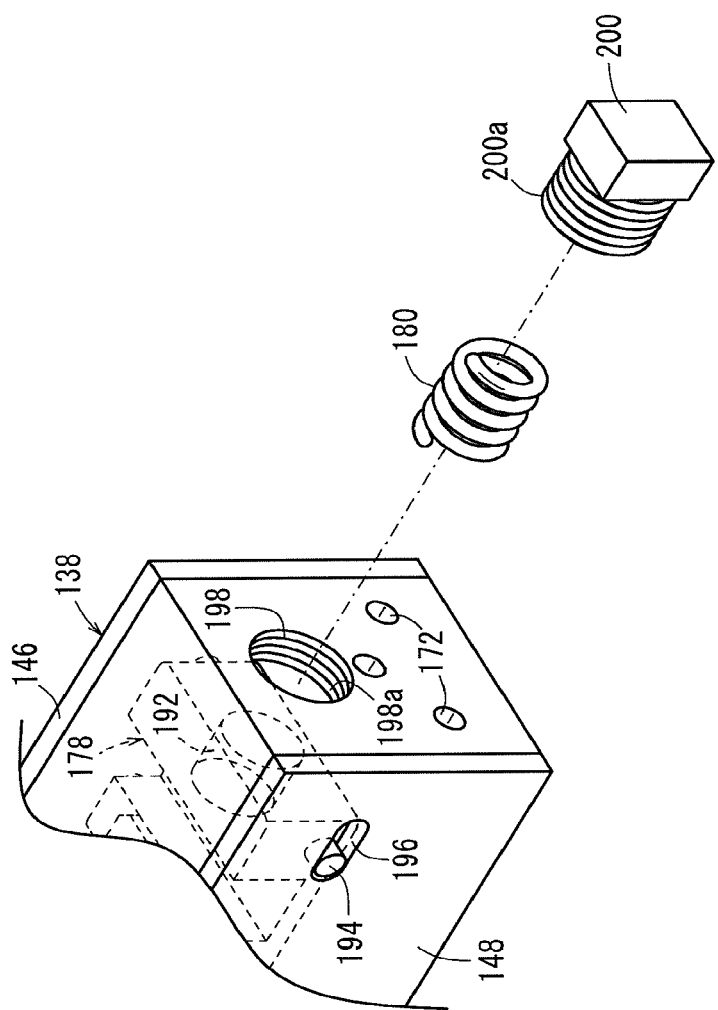
FIG. 11 is a perspective view as seen from a proximal end side of the mechanism unit.

During an assembly step for assembling the mechanism unit 133, as shown in FIG. 11, the elastic member 180 is inserted into the frame 138 in which the slide member 178 is disposed, through the insertion hole 198 from a rearward side of the frame 138. Thereafter, by installing the retaining member 200 in the insertion hole 198, the elastic member 180 can be arranged in a compressed state between the retaining member 200 and the slide member 178.

The retaining member 200 is installed in the insertion hole 198 so as to be capable of changing the amount of compression of the elastic member 180. More specifically, in the present embodiment, female threads 198a are formed on the inner circumferential surface of the insertion hole 198, whereas male threads 200a are formed on the outer circumference of the retaining member 200. Therefore, the retaining member 200 can be screw-engaged in the insertion hole 198. The amount of compression of the elastic member 180 changes corresponding to the amount by which the retaining member 200 is screwed in, whereby the pressing force of the brake shoe 176 applied with respect to the brake rotor 174 can be adjusted.

Next, operations of the brake mechanism 134, which is constructed in the foregoing manner, will be described. With the brake mechanism 134, based on the elastic force of the elastic member 180, a braking force is generated by the brake shoe 176 pressing against the brake rotor 174. More specifically, in a state in which the brake shoe 176 is pressed against the brake rotor 174, rotation of the brake rotor 174 is prevented, and movement of the power transmission mechanism in relation to a tilting operation between the tilt wheel 26 and the distal end working unit 14 also is prevented. Accordingly, during use of the manipulator 10, even in the case that a living tissue (an organ or the like) is pressed by the gripper 12, which has been inserted into the living body, a change in the angle of the gripper 12 with respect to the shaft 18 due to a reaction force from the living tissue is prevented.

In the case of the present embodiment, when the brake shoe 176 is pressed against the brake rotor 174 by the elastic force of the elastic member 180, the first gear 175A provided on the brake rotor 174 and the second gear 175B provided on the brake shoe 176 engage with each other. Therefore, compared to a situation in which the outer circumference of the brake rotor 174 and the brake shoe 176 are both smooth surfaces, due to intermeshing of the gears, a stronger braking force can be obtained. Consequently, even if the elastic force of the elastic member 180 is small, since a sufficient braking force can be obtained, the operating force when braking is released in opposition to the elastic force of the elastic member 180 can effectively be reduced. Accordingly, the manipulator 10 with superior ease of operation can be provided.

Further, in the present embodiment, the slide member 178, which is elastically pressed by the elastic member 180 toward the brake rotor 174 and which is capable of being advanced and retracted with respect to the brake rotor 174, is provided. In addition, the brake shoe 176 is a component that is fixed to the slide member 178. In this manner, the brake shoe 176 is not a member that is formed integrally on a component that is pressed by the elastic member 180, but rather, is a member that is attached to the slide member 178 that is constituted as a separate element. Therefore, in case there is a design modification to the brake shoe 176, since only the brake shoe 176 needs to be modified while leaving the slide member 178 intact, design changes can easily be handled.

Furthermore, in the present embodiment, the second gear 175B extends in an arcuate shape conforming to the outer circumference of the brake rotor 174, and the brake shoe 176 is mounted on the slide member 178 in a state of being capable of swinging slightly with respect to the slide member 178. By such a structure, when the brake shoe 176 abuts against the brake rotor 174, the angle of the brake shoe 176 changes automatically to facilitate meshing of the first gear 175A and the second gear 175B over a predetermined range in the circumferential direction. Accordingly, the brake shoe 176 is aligned and centered automatically with respect to the brake rotor 174, so that a suitable braking force can be exhibited.

In the present embodiment, the insertion hole 198 is disposed in the rear wall 138b of the frame 138, having a size that enables insertion of the elastic member 180 therethrough, and the retaining member 200 is installed in the insertion hole 198. Thus, assembly and removal of the elastic member 180 through the insertion hole 198 can easily and swiftly be carried out. Further, by changing the depth at which the retaining member 200 is screwed in with respect to the insertion hole 198, the amount of compression of the elastic member 180 can be changed, and the force at which the brake shoe 176 presses against the brake rotor 174 can easily be adjusted. Moreover, since a screw-engagement structure is provided, the position of the retaining member 200 can easily be adjusted very finely.

On the other hand, when the brake shoe 176 is distanced from the brake rotor 174 in opposition to the elastic force of the elastic member 180, the braking action performed thereby is released. More specifically, in a state in which the brake shoe 176 is distanced from the brake rotor 174, rotation of the brake rotor 174 is not prevented, and movement of the power transmission mechanism in relation to a tilting operation between the tilt wheel 26 and the gripper 12 is not prevented from occurring. Accordingly, by a rotating operation of the tilt wheel 26, the power thereof is transmitted to the gripper 12, whereby the tilting operation of the gripper 12 is carried out.

Next, the structure of the brake release mechanism 136 will be described. As shown in FIGS. 7 and 8, the brake release mechanism 136 includes release buttons 202 (release operating units) provided on the tilt wheel 26, and lever mechanisms 204 disposed in the tilt wheel 26 and which are pressed by the release buttons 202 being displaced inwardly. Accompanying an inward pressing operation applied with respect to the release buttons 202, the lever mechanisms 204 are operated, whereby the braking action applied by the brake mechanism 134 is released.

The release buttons 202 are disposed in a plurality with intervals therebetween in the circumferential direction on the outer circumference of the tilt wheel 26, in a state of projecting radially outward from the outer circumference. With the present embodiment, nine release buttons 202 are arranged at equal intervals along the outer circumference of the tilt wheel 26.

The tilt wheel 26 includes a disk part 206 to which the wheel shaft 158 is fixed at the center, and a circumferential edge part 208 disposed on the outer edge of the disk part 206 and which projects downwardly from the disk part 206. As shown in FIG. 8, an annular recess 210 is formed on an inner side of the circumferential edge part 208. Further, as shown in FIG. 6, on the circumferential edge part 208, plural button holes 212 (nine are shown in the drawing) are circumferentially disposed at intervals, the button holes 212 penetrating radially through the tilt wheel 26. The release buttons 202 are arranged movably in radial directions respectively in the button holes 212. During the assembly step, the release buttons 202 are inserted from an inner side of the circumferential edge part 208. Plural convex portions 214 and plural concave portions 216 are formed alternately along the circumferential direction on the circumferential edge part 208. The plural release buttons 202 are disposed respectively in the plural concave portions 216. The concave portions 216 are arcuately shaped in the illustrated example.

Engagement tabs 203, which project in substantially opposite directions mutually, are disposed on one end side of each of the release buttons 202. The engagement tabs 203 function as slip-out prevention parts, which prevent slipping-out of the release buttons 202 from the tilt wheel 26. On the inner side of the circumferential edge part 208, a backup member 218 is provided that presses the release buttons 202 outwardly. In the present embodiment, the backup member 218 is a curved plate spring formed in a ring shape having an outer diameter greater than the inner diameter of the circumferential edge part 208 in a natural state, such that in a state of being arranged in the interior of the annular recess 210 of the circumferential edge part 208, both ends of the backup member 218 overlap to form a simple annular shape.

The release buttons 202 are pressed in radially outward directions of the tilt wheel 26 by the backup member 218, which is arranged on the inner side thereof. As a result, the release buttons 202 are prevented from dropping out inwardly from the button holes 212 that are formed in the circumferential edge part 208 of the tilt wheel 26.

Figure 12:
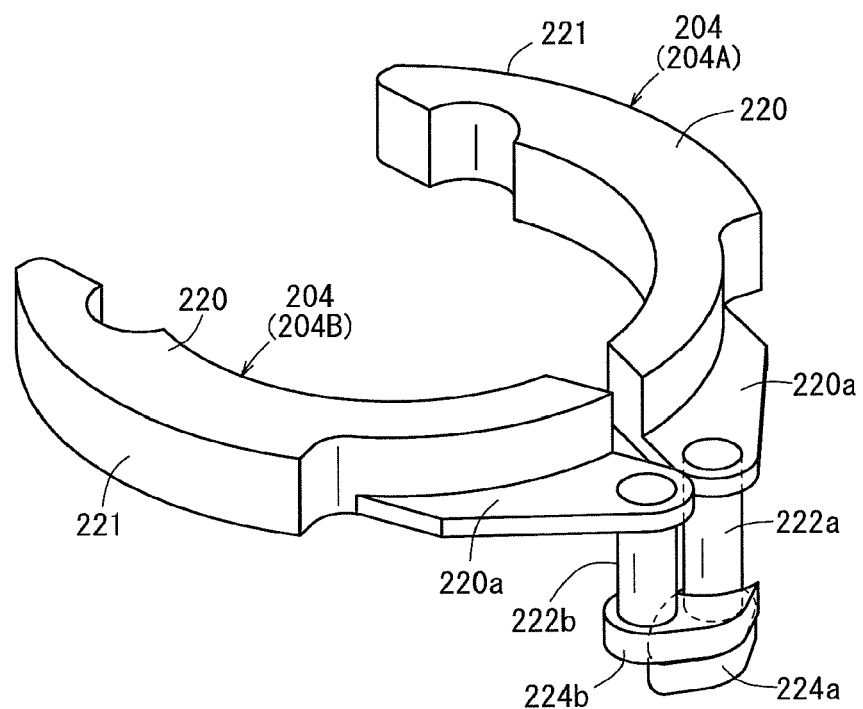
FIG. 12 is a perspective view of a lever mechanism.

As shown in FIGS. 6, 7 and 12, in the present embodiment, the lever mechanisms 204 are disposed as a pair. Below, in cases where the lever mechanisms 204 are distinguished from each other, one of the lever mechanisms 204 will be referred to as a "first lever mechanism 204A", and the other of the lever mechanisms 204 will be referred to as a "second lever mechanism 204B".

As shown in FIG. 12, the lever mechanisms 204 include levers 220 that are pressed and rotated on an inner side of the tilt wheel 26 accompanying inward movement of the release buttons 202, shafts 222a, 222b disposed on the respective levers 220, and cams 224a, 224b that move about the respective shafts 222a, 222b. The levers 220 have curved shapes along the circumferential edge part 208 of the tilt wheel 26, and include arcuately-shaped pressed members 221 provided on outer circumferential sides thereof. The radius of curvature of the pressed members 221 is substantially the same or slightly smaller than the inner diameter of the backup member 218 in a state of being arranged inside the circumferential edge part 208. The levers 220 can receive pressing forces from the release buttons 202, which are positioned on the outer side thereof, within an angular range over which the pressed members 221 are formed. The two levers 220 are of the same shape, and are arranged in laterally symmetrical positions.

As shown in FIG. 12, on each of the levers 220, a base portion 220a is formed on a side opposite from a location on which the pressed member 221 is formed, and to the base portion 220a, a shaft 222a, 222b is connected in a downwardly projecting manner. The two shafts 222a, 222b are supported rotatably in two shaft holes 225, respectively, which are formed in an upper wall portion of the frame 138. The shafts 222a, 222b, which are connected to the respective two levers 220, are of mutually different lengths. In the present embodiment, the shaft 222a of the first lever mechanism 204A is longer than the shaft 222b of the second lever mechanism 204B.

The cams 224a, 224b are formed respectively on lower ends of the shafts 222a, 222b. As shown in FIG. 8, the cams 224a, 224b are arranged in the interior of the frame 138. Below, in cases where the two cams 224a, 224b are distinguished from each other, the cam 224a disposed on the first lever mechanism 204A will be referred to as a "first cam 224a", and the cam 224b disposed on the second lever mechanism 204B will be referred to as a "second cam 224b".

As shown in FIG. 12, the first cam 224a is arranged downwardly from the second cam 224b, and so that the two cams 224a, 224b do not interfere with each other, the two cams 224a, 224b are disposed in mutually overlapping positions as viewed in plan. Further, the second cam 224b has a partially recessed shape such that, at a time of being operated within a movable range thereof, the second cam 224b does not interfere with the shaft 222a of the first lever mechanism 204A. By such a structure, although the shafts 222a, 222b of the first lever mechanism 204A and the second lever mechanism 204B are arranged in close proximity to each other, the cams 224a, 224b do not interfere with each other. Accordingly, the pair of lever mechanisms 204 can be arranged compactly in a narrow space.

As shown in FIG. 7, the two cams 224a, 224b are arranged within the groove 190 that is formed in the slide member 178, in a state of abutment against a central region in the widthwise direction of a front surface of the rear part 186 of the slide member 178. In a state in which the release buttons 202 are not being pressed, the slide member 178, which is biased elastically by the elastic member 180 toward the brake rotor 174, presses against the two cams 224a, 224b. The pressing force received by the cams 224a, 224b acts in a direction to open the two lever mechanisms 204.

The first lever mechanism 204A is operated based on an operation applied with respect to part of the release buttons 202 (in the state shown in FIG. 7, the release buttons 202a, 202b) from among the plurality of release buttons 202. In addition, the second lever mechanism 204B is operated based on an operation applied with respect to other part of the release buttons 202 (in the state shown in FIG. 7, the release buttons 202c, 202d) from among the plurality of release buttons 202. Accordingly, by operating either one of the pair of lever mechanisms 204, the braking action performed by the brake mechanism 134 is released.

Next, operations of the brake release mechanism 136, which is constructed in the foregoing manner, will be described. For releasing the braking action performed by the brake mechanism 134, the release buttons 202 provided on the tilt wheel 26 are pressed inwardly. In this case, although the operator touches only portions of the tilt wheel 26 that are exposed from the openings 27 provided in the casing 29 of the handle main body 20, since the plurality of release buttons 202 are circumferentially arranged on the outer circumference of the tilt wheel 26, the operator can reliably press on the release buttons 202. In addition, when the release buttons 202 are pressed, at least one of the two lever mechanisms 204 (i.e., the levers 220) is pressed through the backup member 218, which is arranged on the inner side of the tilt wheel 26.

In this case, for example, in the event that the release buttons 202 exposed on the right side of the handle 16 are press-operated, the lever 220 of the first lever mechanism 204A is pressed, and the lever 220 is rotated inwardly about the shaft 222a. In the event that the release buttons 202 exposed on the left side of the handle 16 are press-operated, the lever 220 of the second lever mechanism 204B is pressed, and the lever 220 is rotated inwardly about the shaft 222b. Further, when both the release buttons 202 exposed on the right side of the handle 16 and the release buttons 202 exposed on the left side of the handle 16 are press-operated, the lever 220 of the first lever mechanism 204A and the lever 220 of the second lever mechanism 204B are both pressed and rotated inwardly.

Accompanying rotation of one or both of the first lever mechanism 204A and the second lever mechanism 204B, the cams 224a, 224b press and displace the slide member 178 in an opposite direction to the brake rotor 174 (rearwardly of the manipulator 10 in the illustrated example) in opposition to the elastic force of the elastic member 180. Along with displacement of the slide member 178, the brake shoe 176 that is mounted on the slide member 178 also is displaced in unison with the slide member 178. In this case, any one of the two cams 224a, 224b comes into contact with the central region in the widthwise direction of the slide member 178. Consequently, even in the case that only one of the two lever mechanisms 204 is rotated, since either one of the cams 224a, 224b presses the central region in the widthwise direction of the slide member 178, the slide member 178 can be displaced smoothly.

Accompanying displacement of the slide member 178, the brake shoe 176 separates away from the brake rotor 174, and the brake rotor 174 assumes a state in which rotation thereof is enabled. More specifically, a state is brought about in which the braking action performed by the brake mechanism 134 is released. Consequently, under a condition in which the release buttons 202 are pressed, the operating force is applied to the tilt wheel 26 in the direction of rotation of the tilt wheel 26, whereby the tilt wheel 26 can be rotated, and a tilting operation can be effected to the gripper 12. In this case, since the release buttons 202 rotate integrally with the tilt wheel 26, while the inwardly-pressed condition of the release buttons 202 is maintained, the rotating operation of the tilt wheel 26 can easily be carried out.

In this manner, according to the brake release mechanism 136, since the release buttons 202 for releasing the braking action are provided on the tilt wheel 26, which is operated to carry out a tilting operation on the gripper 12, the operator of the manipulator 10 can easily contact and touch the release buttons 202 with the same hand that operates the tilt wheel 26. Accordingly, the braking action performed by the brake mechanism 134 can easily and swiftly be released with one hand. More specifically, the brake releasing operation and the rotating operation of the tilt wheel 26 can both be carried out easily and reliably with one hand.

Further, since the levers 220, which are pressed accompanying an operation performed with respect to the release buttons 202, are arranged on the inner side of the tilt wheel 26, the brake release mechanism 136 can be constructed compactly, and can contribute to a reduction in size and weight of the manipulator 10 in which the brake mechanism 134 is incorporated.

In the present embodiment, the lever mechanisms 204 include the levers 220 that are pressed and rotated on an inner side of the tilt wheel 26 accompanying inward movement of the release buttons 202, the shafts 222a, 222b disposed on the levers 220, and the cams 224a, 224b that are moved about the shafts 222a, 222b. In addition, accompanying an operation performed with respect to the release buttons 202, the cams 224a, 224b are operated so as to cause the brake shoe 176 to separate away from the brake rotor 174, whereby the braking action is released. Owing to such a structure, by appropriately setting the lever ratio of the lever mechanisms 204, releasing of the braking action can be implemented with a low operating force.

In the case of the present embodiment, since the two lever mechanisms 204 are provided, and releasing of the braking action is performed by actuating either one of the lever mechanisms 204, the brake releasing operation can be carried out more easily and reliably.

Further, in the present embodiment, the release buttons 202 are disposed displaceably in inward and outward directions on the outer circumference of the tilt wheel 26. In accordance with this structure, since the braking action can be released by press-gripping the release buttons 202 inwardly, and in this condition, the tilt wheel 26 can be rotated, a series of operations including the brake-releasing operation and thereafter the rotating operation can smoothly be carried out without interruption.

Furthermore, in the present embodiment, since the backup member 218 that presses the release buttons 202 outwardly is provided on the inner side of the tilt wheel 26, release buttons 202 that are located at positions that do not correspond to the levers 220 are prevented from falling out from the tilt wheel 26.

In the present embodiment, the release buttons 202 are disposed respectively at a plurality of different positions in the circumferential direction on the outer circumference of the tilt wheel 26. According to such a structure, since not only one but multiple release buttons 202 are provided, releasing of the braking operation can be performed easily merely by the user selecting and pressing any of the release buttons 202 that can easily be gripped.

In the present embodiment, plural convex portions 214 and plural concave portions 216 are each formed alternately along the circumferential direction on the outer circumferential part of the tilt wheel 26, and the plural release buttons 202 are disposed respectively in the plural concave portions 216. By such a structure, since the release buttons 202 are arranged at positions where they are not easily pressed simply by touching the tilt wheel 26 accidentally, unintentional releasing of the braking action can effectively be inhibited.

Although certain preferred embodiments of the present invention have been shown and described in detail above, it should be understood that the present invention is not limited to the embodiment, and various changes and modifications may be made to the embodiments without departing from the scope of the invention as set forth in the appended claims.

What is claimed is:

1. A medical manipulator equipped with a distal end working unit on a distal end of a shaft that extends from a handle, the distal end working unit being capable of being tilted with respect to the shaft, the medical manipulator being constituted so as to mechanically transmit an input operation with respect to a tilt wheel provided on the handle to thereby tiltably operate the distal end working unit, and further being equipped with a brake mechanism, wherein the brake mechanism comprises:

a brake rotor that rotates in conjunction with rotation of the tilt wheel; and a brake shoe, which is capable of advancing and retracting with respect to the brake rotor, and is capable of contacting an outer circumference of the brake rotor, wherein:

based on an elastic force of an elastic member, the brake shoe is pressed against the brake rotor to thereby generate a braking force;

a braking action is released by separating the brake shoe away from the brake rotor in opposition to the elastic force;

a first gear is disposed along a circumferential direction on the outer circumference of the brake rotor; and a second gear, which is capable of meshing with the first gear, is disposed on a portion of the brake shoe that confronts the outer circumference of the brake rotor;

wherein the brake rotor is a member that rotates in conjunction with rotation of the tilt wheel; and based on the elastic force of the elastic member, the brake shoe is pressed against the brake rotor, whereby rotation of the brake rotor is prevented, and an angle of the distal end working unit with respect to the shaft is fixed.

2. The medical manipulator according to claim 1, wherein:

the second gear extends in an arcuate shape conforming to the outer circumference of the brake rotor; and the brake shoe is mounted on the slide member in a state of being capable of swinging slightly with respect to the slide member.

3. The medical manipulator according to claim 2, wherein:

the second gear extends in an arcuate shape conforming to the outer circumference of the brake rotor; and the brake shoe is mounted on the slide member in a state of being capable of swinging slightly with respect to the slide member.

4. The medical manipulator according to claim 2, wherein:

the brake rotor, the brake shoe, and the slide member are arranged inside a frame;

on a wall of the frame that is formed on an opposite side from the brake rotor with the slide member interposed therebetween, an insertion hole is disposed having a size that allows the elastic member to be inserted therethrough; and a retaining member that holds and presses the elastic member is installed in the insertion hole.

5. The medical manipulator according to claim 4, wherein the retaining member is installed in the insertion hole so as to be capable of changing an amount of compression of the elastic member.

6. A medical manipulator, comprising:
a handle;
a shaft extending from the handle;
a working unit on a distal end of the shaft, the working unit configured to tilt with respect to the shaft,
a tilt wheel provided on the handle and configured to mechanically transmit an input operation to thereby tiltably operate the working unit;
a brake mechanism comprising:
- a brake rotor configured to rotate in conjunction with rotation of the tilt wheel; and
- a brake shoe configured to advance and retract relative to the brake rotor, and configured to contact an outer circumference of the brake rotor, wherein:
- an elastic member configured to press, via an elastic force, the brake shoe against the brake rotor to thereby generate a braking action that prevents rotation of the brake rotor and fixes an angle of the working unit with respect to the shaft;
- a first gear disposed along a circumferential direction on the outer circumference of the brake rotor; and
- a second gear disposed on a portion of the brake shoe that confronts the outer circumference of the brake rotor, the second gear configured to mesh with the first gear;
wherein a braking action is released by separating the brake shoe away from the brake rotor in opposition to the elastic force.

* * * * *